United States Patent [19]

Laguette et al.

[11] Patent Number: 5,152,753
[45] Date of Patent: Oct. 6, 1992

[54] MEDICATION INFUSION DEVICE WITH DOSE RECHARGE RESTRICTION

[75] Inventors: Stephen W. Laguette, Goleta; Gary P. East, Santa Barbara; David A. Watson, Goleta; Thomas J. Carlisle, Santa Barbara, all of Calif.

[73] Assignee: Pudenz-Schulte Medical Research Corporation, Goleta, Calif.

[21] Appl. No.: 503,426

[22] Filed: Apr. 2, 1990

[51] Int. Cl.⁵ .............................................. A61M 1/00
[52] U.S. Cl. .................................. 604/153; 604/890.1
[58] Field of Search ...................... 604/93, 153, 891.1, 604/140, 890.1, 181, 183, 185, 186; 128/DIG. 12

[56] References Cited

U.S. PATENT DOCUMENTS

| | | |
|---|---|---|
| 342,131 | 6/1886 | Perkins et al. . |
| 3,503,402 | 3/1970 | Schulte . |
| 3,527,220 | 9/1970 | Summers . |
| 3,756,243 | 9/1973 | Schulte . |
| 3,768,508 | 10/1973 | Schulte . |
| 3,827,439 | 8/1974 | Schulte . |
| 4,360,019 | 11/1982 | Portner et al. . |
| 4,364,395 | 12/1982 | Redmond et al. . |
| 4,544,371 | 10/1985 | Dormandy, Jr. et al. . |
| 4,552,553 | 11/1985 | Schulte et al. . |
| 4,557,721 | 12/1985 | Hooven . |
| 4,557,722 | 12/1985 | Harris . |
| 4,560,375 | 12/1985 | Schulte et al. . |
| 4,588,394 | 5/1986 | Schulte et al. . |
| 4,634,427 | 1/1987 | Hannula et al. . |
| 4,668,231 | 5/1987 | de Vries et al. ................. 604/891.1 |
| 4,681,560 | 7/1987 | Schulte et al. . |
| 4,681,564 | 7/1987 | Landreneau . |
| 4,681,570 | 7/1987 | Dalton . |
| 4,857,059 | 8/1989 | Rey et al. . |
| 4,898,582 | 2/1990 | Faste . |
| 4,898,583 | 2/1990 | Borsanyi et al. . |
| 4,898,584 | 2/1990 | Borsanyi et al. . |
| 4,898,585 | 2/1990 | Borsanyi et al. . |

FOREIGN PATENT DOCUMENTS 664424 9/1965 Belgium .

OTHER PUBLICATIONS

Miley, *Direct Conversion of Nuclear Radiation Energy*, pp. vii–xi and 95–111, American Nuclear Society, Champaign, Ill. (1976).
Title: Implantable Devices for Drug Delivery to the Circulatory and Central Nervous Systems, Author: Robert H. Pudenz, M.D. 42 pages.
Title: N.Y.U. Volume Control Valve drawing.

*Primary Examiner*—Paul J. Hirsch
*Attorney, Agent, or Firm*—Kelly, Bauersfeld & Lowry

[57] ABSTRACT

A subcutaneously implantable medication infusion device includes a variable capacity reservoir for receiving and storing fluid medication for delivery to a catheter which directs the medication to a specific infusion location in the body. A control assembly is interposed between the reservoir and the catheter to facilitate and control the transfer of the medication from the reservoir to the catheter in a safe and efficient manner. The control assembly includes a self-recharging pump and a normally closed valve, both of which are manually actuable by percutaneous pressure when subcutaneously implanted, and defines a portion of a fluid flow conduit between the reservoir and the catheter. The control assembly is constructed to permit the infusion of a measured bolus of medication on demand through manual percutaneous manipulation of the control assembly. A restrictor is provided the control assembly to limit the rate the pump is recharged with medication, to restrict the total amount of medication which can be pumped into the catheter over a given period of time. In one preferred form, the pump recharge restriction is created by providing at least one capillary-like fluid pathway through which the recharge fluid must pass before entering the pump. In another preferred form of the invention, the recharge flow rate of medication into the pump is restricted by a wick restrictor.

42 Claims, 4 Drawing Sheets

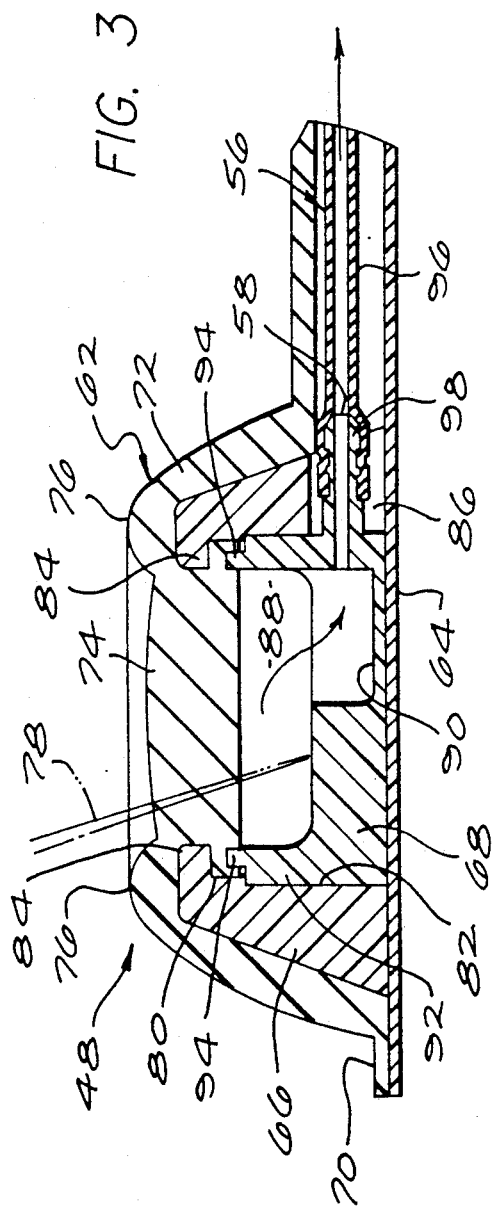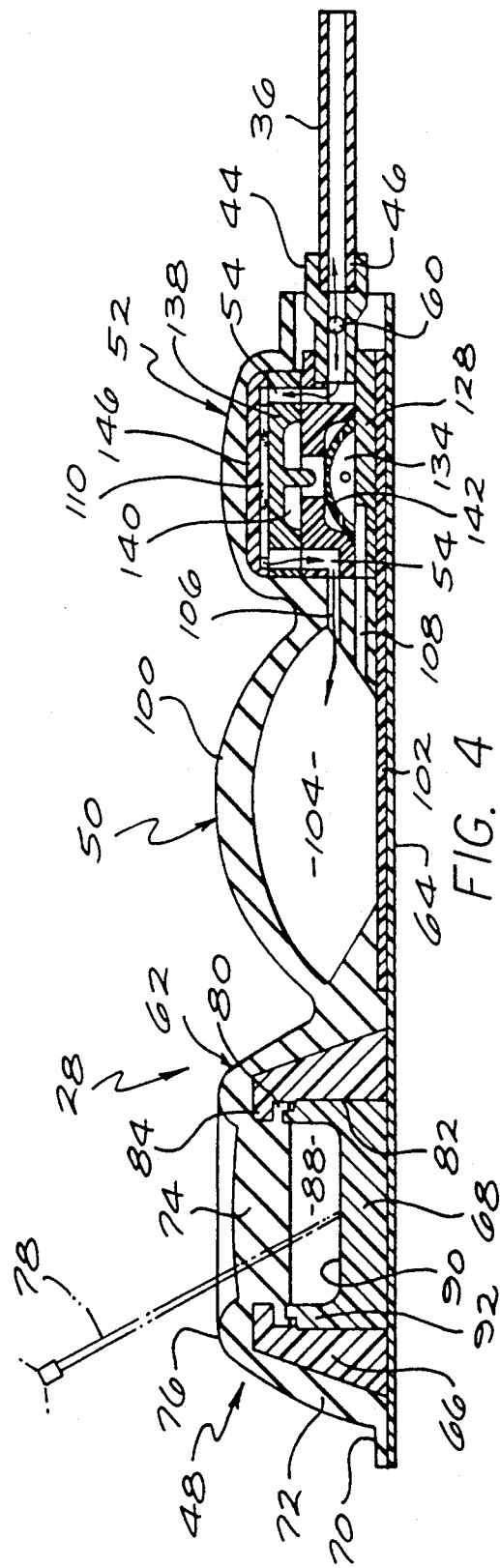

MEDICATION INFUSION DEVICE WITH DOSE RECHARGE RESTRICTION

BACKGROUND OF THE INVENTION

This invention relates generally to infusion systems for the administration of medications. More particularly, the present invention relates to a refillable and subcutaneously implantable medication delivery system including means for limiting the total amount of medication which can be infused therethrough over a given period of time.

It has been found in the treatment of several various medical conditions that the administration of medications over sustained periods of time is necessary. For instance, it is often desirable to provide a pain killer, such as morphine, to terminally ill patients to help them cope with the sometimes excruciating pain which accompanies certain diseases. Frequently terminally ill patients experience such extreme pain that hospitalization becomes necessary to provide medications at intervals and in quantities sufficient to meet the patient's needs. Alternatively, when hospitalization is not acceptable the patient is often required to obtain private nursing care.

Requiring a terminally ill patient to either be hospitalized or to arrange for private nursing care can result in substantial burdens being imposed upon both the health care system and the patient. Health care facilities are increasingly burdened as the demand for hospital bed space increases at a rate greater than the growth in available bed space. This burden is accentuated when patients, such as terminally ill patients, are hospitalized for want of an alternative treatment methodology. Also, the diversion of medically trained personnel to deal with the routine infusion of medications imposes additional burdens on the health care system which could be avoided provided the proper technology were available.

When patients must be confined to a hospital bed or arrange for private duty nursing care to receive prescribed medications, the costs involved often exceed the financial means of such patients. For example, many terminally ill patients cannot afford to pay for the expensive and individualized care which could make the last period of time prior to death much more productive and less difficult for the patient and for those around him. Indeed, some patients cannot afford any medical care whatsoever and their only available alternative is to forego treatment. Sometimes patients who cannot afford the hospitalization or private nursing care required and who cannot tolerate the pain involved with a particular disease must be hospitalized at society's expense.

These burdens to the patient, the health care system and to society in general have prompted several changes in health care methodology. For instance, many physicians have found it desirable to administer prescribed medications on an out-patient basis. This out-patient technique has proven to be effective in substantially reducing the costs associated in the treatment of many types of ailments; however, there have been a number of drawbacks which have made such out-patient arrangements less than ideal.

A typical drawback of out-patient treatment programs includes the requirement of frequent visits by the patient with the physician and the resultant time and transportation problems. It is recognized that if the patient could be provided adequate home care for extended periods of time, the time between visits with the physician could be lengthened. Such extended home care would benefit the physician, as well as the patient in many circumstances, by permitting the physician to devote more professional time to other important matters.

Notwithstanding the foregoing, some patients find that receiving regular injections of medication over a prolonged period of time is distasteful, not to mention painful. It has been found that repeated injections through the skin into a specific, limited area of the body can be harmful to the patient and can sometimes cause problems which could become more threatening to the well-being of the patient than the illness being treated. Such problems have made necessary the use of alternate injection sites, the rotation of injections among alternate injection sites, or, the extreme, the abandonment of medication injections as a useful form of treatment.

Moreover, some substances have been found to traumatize the skin when injected, and this has necessitated the use of alternative means for introducing such substances into the body. Such alternate introduction means have included the use of catheters which are inserted through the skin into the body and have a portion which remains extended through the patient's skin to provide external access. This and similar methods and systems have proven to be undesirable for extended treatment because of the risk of infection at the incision site where the catheter extends through the skin.

In an effort to overcome the above-noted drawbacks with prior treatment procedures, several types of drug delivery devices have been developed which permit the self-administration of medication in precise quantities while minimizing the number of injections required and visits which need be made with a physician. Exemplary of such prior drug delivery devices are those illustrated in U.S. Pat. Nos. 4,588,394 and 4,681,560, the contents of which are incorporated herein by reference. These prior systems are constructed for total subcutaneous emplacement in the body, include appropriate devices to prevent the unintended infusion of the medication from the system into the body, and are refillable, such as by injection, to permit long term use. Such devices may be applicable not only in the administration of medication to terminally ill patients, but also in the administration of other medications, such as insulin to diabetic patients.

In the development of such infusion systems which are totally subcutaneously emplaced in the body and which are actuated by manual percutaneous manipulation, some medical professionals have worried that such devices may pose danger to the patient since the medication is self-administered. In the case of a terminally ill patient, there is a danger that the patient or another giving care to the patient may infuse too great a quantity of a substance such as morphine through the system, in the absence of suitable safeguards. Similarly, in the case of diabetic patients, there is a danger, or at least the possibility, that too great a quantity of insulin could be self-administered through implantable and manually self-actuable systems and devices.

In efforts to ensure that medication is not accidentally infused into the patient, prior systems are usually designed to require at least two positive percutaneous manipulative steps before medication is permitted to pass into a delivery catheter for infusion into the body.

The above-referenced patents show good examples of prior devices incorporating such safeguards. Some medical professionals have opted not to give the patient the opportunity to self-administer medication, but regulate the rate of medication infusion through systems powered by internal batteries or external power sources.

Accordingly, there has been a need in the medical arts for an infusion system which allows the patient to administer required medications in precise quantities while minimizing the number of injections required and visits which need be made with a physician. Such an infusion system is needed which inherently limits the amount of medication which can be infused into the patient over a given period of time. Preferably, such limitation on the total amount of medication which can be infused over a given period of time can be accomplished independently of the size of a reservoir for storing the medication. Further, a novel medication delivery device is needed which may be totally subcutaneously emplaced in the body, includes appropriate devices to prevent the unintended infusion of the medication from the system to the body, is refillable by injection to permit long-term use, and includes an inherent recharge restriction capability for limiting the rate at which medication may be infused to the body while preserving the ability of the patient to self-administer the medication on demand in a safe and reliable manner. Moreover, a novel process is needed for percutaneously controlling the flow of fluid through a subcutaneously implanted infusion system including a manually actuable pump and a valve for controlling the flow of fluid from the pump. The present invention fulfills these needs and provides other related advantages.

SUMMARY OF THE INVENTION

The present invention resides in a medication infusion device useful, for example, in the administration of medication to a patient requiring infusions of medication at relatively frequent intervals and over extended periods of time. More particularly, the present invention resides in a medication infusion system which is totally subcutaneously implanted in the patient, and is manually actuated by the application of percutaneous pressure to infuse a measured bolus of medication on demand. The infusion system comprises, generally, means for receiving medication into the system by injection, a reservoir fluidly connected to the receiving means in a manner permitting the subcutaneous transfer of medication from the receiving means to the reservoir, and a delivery catheter for directing the medication to a specific location in the body. Means are provided for conducting the medication from the reservoir to the catheter inlet. Further, means are provided for controlling the flow of medication from the reservoir to the catheter, forming a portion of the conducting means, which include a normally closed valve and a pump for flushing a measured quantity of medication into the catheter when the normally closed valve is opened. Moreover, means are provided for restricting the flow of medication from the reservoir to the pump, and thus limiting the rate the pump is recharged, to restrict the total amount of medication which can be pumped into the catheter over a given period of time.

In a preferred form of the invention, the controlling means comprises a subcutaneously implantable medication infusion control assembly having a medicament recharge restriction. The control assembly includes a self-recharging, manually actuable pump for discharging a measured amount of fluid from a pumping chamber. The pump includes a pump inlet in fluid communication with the reservoir, a pump outlet in fluid communication with the normally closed valve, and a resilient crown overlying a floor plate to define the pumping chamber therebetween. Means are provided for conducting pump recharge fluid from the receiving means and the reservoir into the pumping chamber, and means are provided for conducting discharge fluids from the pumping chamber to the catheter.

The control assembly also includes a normally closed valve which is actuable by manual percutaneous manipulation for controlling the flow of discharge fluid from the pumping chamber. The normally closed valve forms a portion of the discharge fluid conducting means and includes a resiliently flexible body which defines a fluid flow passageway therethrough. A valve member is positioned within the fluid flow passageway to occlude the valve. The normally closed valve further includes a valve inlet in fluid communication with the pump outlet, a valve outlet in fluid communication with the catheter inlet, and a valve passageway situated directly between the valve inlet and outlet. The valve member is resiliently biased to occlude the valve passageway, and a displacement finger is situated and configured within the valve to displace the valve member and open the valve to fluid flow therethrough when actuated by manual percutaneous pressure.

The control assembly is further provided with means for restricting the rate of fluid flow through the recharge fluid conducting means. The restricting means effectively limits the amount of recharge fluid permitted to enter the pumping chamber over a given period of time. In one preferred form, the restricting means includes at least one capillary-like fluid pathway through which the recharge fluid must pass before entering the pumping chamber. When the capillary-like fluid pathway restrictor is utilized, the restricting means is positioned relative to the displacement finger so that manipulation of the normally closed valve to move the displacement finger, which opens the discharge fluid conduit means, occludes the capillary-like fluid pathway restrictor to occlude the recharge fluid conducting means.

In another embodiment of the invention, the restricting means includes a wick restrictor having a plurality of wicking fibers situated within an impermeable wick housing. The wick restrictor is positioned within a portion of the recharge fluid conducting means so that all fluid drawn into the pumping chamber must first pass through the wick restrictor. One end of the wick housing is occluded, and an inlet is provided adjacent to the occluded end through a wall of the wick housing.

The means for receiving medication into the system by injection comprises an injection port including, generally, an elastomeric outer housing having an integral elastomeric septum, a pair of base members situated within the outer housing and which compress a portion of the septum therebetween, and an outlet. The outlet extends from an internal chamber between the septum and the base members, exteriorly through the outer housing.

Another aspect of the present invention involves a novel process for infusing medication stored within a subcutaneously implanted infusion system. In accordance with this aspect of the invention, a process for percutaneously controlling the flow of fluid through a subcutaneously implanted infusion system including a manually actuable pump having a pump inlet and a pump outlet, and a valve for controlling the flow of fluid from the pump, comprises a number of novel process steps.

Specifically, the valve is opened by applying percutaneous pressure thereto, to permit medication in the pump to be discharged through the pump outlet. The step of opening the valve includes pressing a housing of the valve downwardly. The pump inlet is occluded to prevent medication from entering the pump when the valve is opened. The steps of opening the valve and occluding the pump inlet are accomplished simultaneously through the application of the percutaneous pressure to the valve.

Medication in the pump is discharged through the pump outlet and the valve by applying percutaneous pressure to the pump. This is accomplished by pressing a housing of the pump downwardly to flush fluid from a pump chamber within the pump, wherein the step of flushing fluid from the pump occurs only after the valve is opened.

After the medication has been discharged from the pump, the valve is closed by removing the percutaneous pressure applied thereto, and the pump inlet is opened to permit fluid flow into the pump when the valve is closed. The steps of closing the valve and opening the pump inlet are accomplished simultaneously through the withdrawal of percutaneous pressure from the valve.

The rate at which fluid can flow into the pump through the pump inlet is restricted in order to limit the amount of fluid which can be pumped through the infusion system over a given time period. In accordance with one preferred method, fluid stored in the infusion system is caused to pass through a capillary-like fluid pathway as the fluid is drawn into the pump. The capillary-like fluid pathway severely restricts the rate at which fluid would otherwise flow into the pump, to a known flow rate that limits the maximum amount of fluid which can be pumped through the system over a given time period. The capillary-like fluid pathway is closed to fluid flow when percutaneous pressure is applied to the valve.

In accordance with another preferred method, fluid stored in the infusion system is caused to pass through a plurality of packed wicking fibers. The wicking fibers are placed in a fluid flow conduit between the pump and the stored medication, and the medication is introduced at the wicking fibers perpendicularly to their length.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 3 is an enlarged fragmented sectional view taken generally along the line 3—3 of FIG. 2, illustrating the construction of an injection port portion of the control assembly, and the manner in which medication may be injected through a septum of the injection port;

FIG. 4 is an enlarged sectional view of the control assembly taken generally along the line 4—4 of FIG. 2, illustrating a recharge fluid flow path through a valve portion of the control assembly to a pump portion;

DETAILED DESCRIPTION OF THE PREFERRED EMBODIMENT

Figure 1:
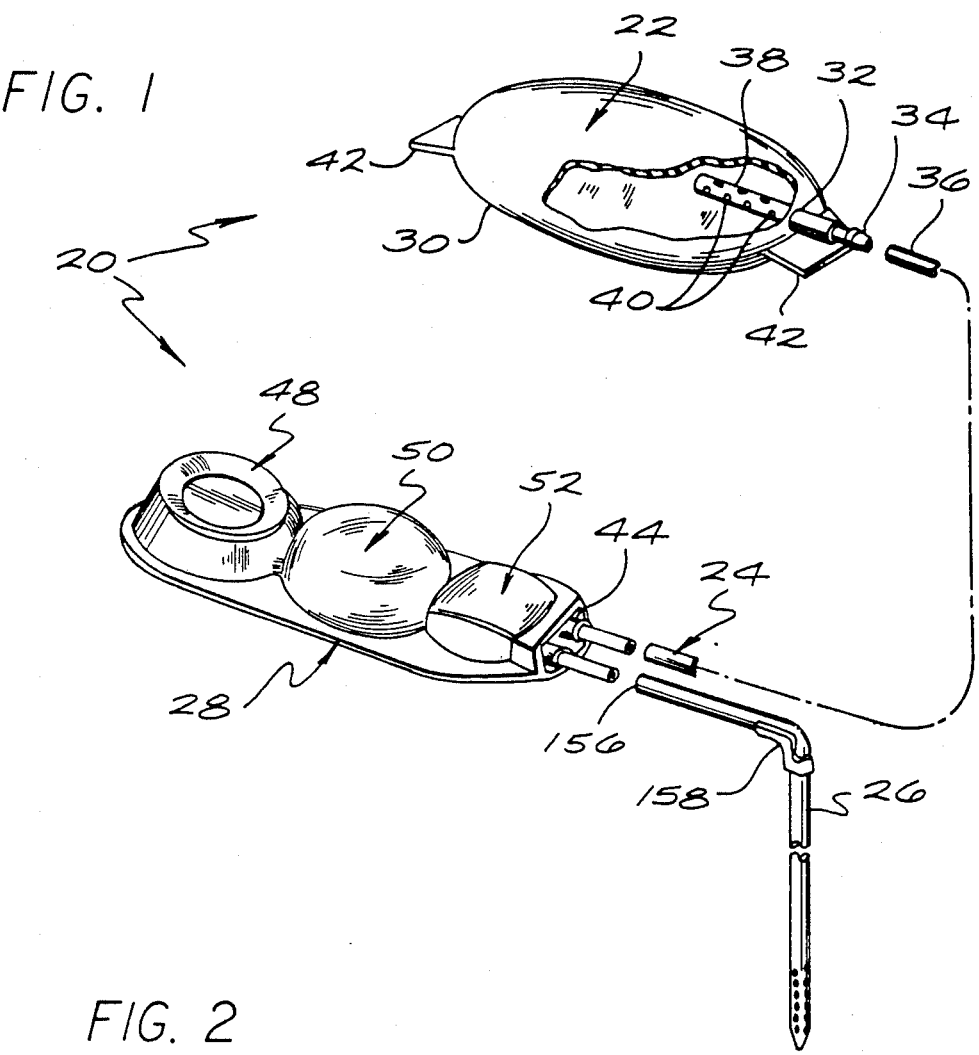
FIG. 1 is a partially fragmented perspective diagrammatic view of a preferred form of the medication infusion device of the present invention, illustrating the relationship of the various components of the infusion device to one another, and specifically the relationship of a control assembly relative to a reservoir and a delivery catheter, wherein a portion of the reservoir shell is broken away for illustrative purposes only.
Figure 2:
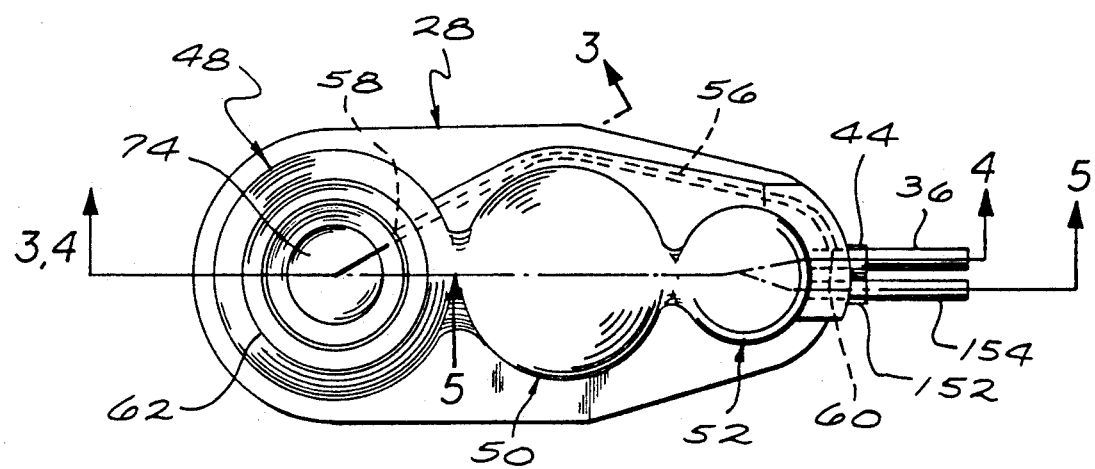
FIG. 2 is an enlarged top plan view of the control assembly illustrated in FIG. 1.
Figure 5:
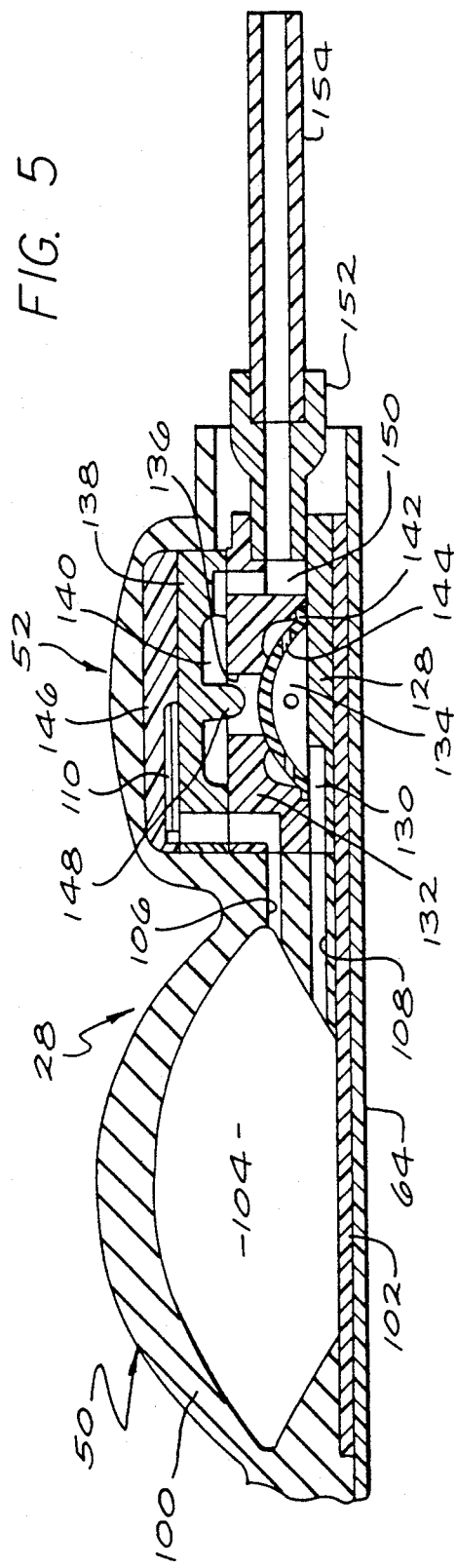
FIG. 5 is an enlarged fragmented sectional view of a portion of the control assembly taken generally along the line 5—5 of FIG. 2 illustrating, particularly, a discharge fluid pathway from the pump through the valve for infusion as directed by the catheter.

As shown in the drawings for purposes of illustration, the present invention is concerned with an improved medication infusion system, generally designated in the accompanying drawings by the reference number 20. As illustrated best in FIG. 1, the medication infusion system 20 generally comprises a variable capacity reservoir 22 connected by a fluid flow conduit 24 to a catheter 26 which directs medications stored in the reservoir to a specific location within a patient. A fluid flow control assembly 28 is provided to prevent or reduce the likelihood of an inadvertent infusion into the patient of medication stored in the reservoir 22.

The control assembly 28 used in the system 20 is situated between the reservoir 22 and the catheter 26 to form a portion of the fluid flow conduit 24. The system 20 requires fluid medication to flow through the control assembly 28 before passing into the catheter 26. With the safety and well-being of the patient and all-important consideration in the employment of the system 20, this flow path requirement provides the control over the flow of medication which is critical to the system's safe use. Indeed, the control assembly 28 virtually eliminates the chance of inadvertently infusing more than a very small quantity of medication into the patient by requiring specific sequential and deliberate steps to be taken before a measured volume of fluid can be pumped through the system 20.

The medication infusion system 20 can substantially reduce the cost of treating some illnesses by eliminating the need for constant medical attention or by reducing the number of required visits which need be made with a physician. The overall design of the system 20 permits construction into a variety of configurations for use in many types of different applications. The system 20 may be used advantageously by patients requiring regular infusions by minimizing the number of injections received. As will be discussed in greater detail below, the medication infusion system 20 of the present invention includes means for limiting the maximum amount of medication which can be pumped through the system over a given time period.

In accordance with the present invention, and as illustrated with respect to one preferred embodiment in FIGS. 1 through 8, the variable capacity reservoir 22 comprises a silicone elastomer shell 30 which can expand and collapse to accommodate changing volumes of fluid medication. The reservoir 22 includes an outlet aperture 32 and an outlet connector 34 secured within the aperture 32. The outlet connector 34 is designed to engage one end of a first segment of surgical tubing 36 which extends between the reservoir 30 and the control assembly 28.

A flexible tube 38 having a plurality of tube apertures 40 extends from the reservoir aperture 32 generally rearwardly into the center of the reservoir 22. The flexible tube 38 is preferably constructed of a silicone elastomer material having sufficient resiliency to maintain a fluid passageway through its center for channeling fluid medication from the reservoir 22 through the aperture 32 and into the first segment of surgical tubing 36, notwithstanding a collapse of the reservoir shell 30. Specifically, the flexible tube 38 ensures that fluid medication will be able to exit the reservoir 22 even when the reservoir shell 30 collapses in a manner that would otherwise cover the reservoir outlet aperture 32. Such a collapse of the reservoir shell 30 may result from an emptying of fluid from the reservoir 22 during use of the system 20.

In systems 20 designed for use in the treatment of terminally ill patients, a reservoir 22 having a thirty milliliter capacity would normally hold sufficient amounts of morphine or other similar pain killing drugs to supply patients sufficient quantities of medication for several days. The variable capacity reservoir 22 can be remotely located from the insertion point of the catheter 26 in any suitable position as the surgeon chooses, such as in the abdominal cavity, below the ribs or near the clavicle. Indeed, the reservoir 22 can be placed in any soft area of the body which would permit the reservoir to be percutaneously grasped while subcutaneously implanted. To aid in the positioning of the reservoir 22, suture tabs 42 are integrally formed with the reservoir shell 30 to permit the surgeon to anchor the reservoir 22 at the selected location within the patient to prevent migration of the reservoir to an undesirable location.

The first segment of surgical tubing 36 extends from the outlet connector 34 of the reservoir 22, to a first port 44 of the control assembly 28. An end 46 of the surgical tubing 36 is fixed within the first port 44 (FIGS. 1, 2 and 4) in any suitable manner which prevents separation of the first segment of surgical tubing 36 from the control assembly 28.

The control assembly 28 includes three primary components: an injection port 48, a pump 50 and a normally closed valve 52. A recharge fluid flow passageway 54 is provided through the control assembly 28 to direct recharge fluid from the first port 44 to the pump 50. The control assembly 28 also provides an injection port fluid outlet passageway 56 between an outlet 58 of the injection port 48, and the recharge fluid flow passageway 54. The fluid passageways 54 and 56 intersect, within the control assembly 28, at a port 60 situated generally adjacent to the first port 44 of the control assembly 28.

The injection port 48 shown in the accompanying drawings (FIGS. 1 through 4) is constructed as part of the control assembly unit 28. The injection port 48, however, could be manufactured as a separate component apart from the pump 50 and the normally closed valve 52, since it does not directly interrelate with the function of the pump and the normally closed valve. The injection port 48 comprises an upper elastomeric dome 62, a lower elastomeric reinforced sheet 64 which generally underlies the entire control assembly 28, and a pair of base members 66 and 68 housed within the dome 62 above the reinforced sheet 64. The upper dome 62 includes a lower flange 70 which is directly sealed to the reinforced sheet 64 by means of a standard adhesive. Accordingly, the dome 62 and reinforced sheet 64 present a continuous elastomeric outer housing for the injection port 48, which helps prevent leakage of drugs injected into the injection port 48 when subcutaneously implanted.

Extending upwardly from the dome flange 70 is a frusto-conical side wall 72 which supports an integrally formed septum 74 in a spaced relation above the lower reinforced sheet 64. The upper end of the side wall 72 surrounding the septum 74 provides means for percutaneously manually locating the septum when the injection port 48 is subcutaneously implanted. More particularly, the side wall 72 includes a ridge 76 which circumscribes an upper exterior surface of the septum 74. The dome 62 is further provided with an outlet connector passageway through a lower portion thereof.

The septum 74 comprises a thickened portion of silicone elastomer material having characteristics which permit repeated intermittent puncture by a needle 78 for injection of medication from a syringe. Such a needle 78 is preferably twenty-gauge or smaller. The septum 74 includes a septum flange 80 which generally circumscribes a lower end of the septum beneath the ridge portion 76 of the side wall 72. The septum flange 80 defines a flange-receiving cavity into which a portion of the outer base member 66 is positioned.

The outer base member 66 is preferably formed of a rigid polypropylene material and includes a generally frusto-conical ring 82 configured to contiguously engage and support the interior surface of the dome side wall 72. The outer base member 66 further includes a rigid upper flange 84 configured to fit within the flange receiving cavity of the dome 62, and circumscribe the septum 74 and engage the septum flange 80. More particularly, the rigid upper flange 84 of the outer base member 66 overlies the septum flange 80 and provides a rigid barrier between the septum flange and the adjacent portions of the dome side wall 72. Below the rigid upper flange 84 of the outer base member 66, the interior of the ring 82 forms an inner cylindrical surface dimensioned to receive and firmly hold the inner base member 68 in an interference fit therein. The outer base member 66 further includes an outlet connector passageway 86 in the lower end of the ring 82, which is aligned with the outlet connector passageway of the elastomeric dome 62.

The inner base member 68 is preferably formed of a rigid polypropylene material and when positioned within the outer base member 66 it defines, with the septum 74, an internal injection chamber 88. The inner base member 68 is generally cup-shaped and includes a floor 90 and a continuous wall 92 which extends upwardly from the floor 90. The floor 90 and the wall 92 effectively form a needle shield which prevents the needle 78 from passing completely through the injection port 48 after it has entered the injection chamber 88. An upper septum-engaging section 94 extends upwardly from the upper edge of the continuous wall 92 and, in the assembled configuration, engages the underside of the septum flange 80. The upper septum-engaging section 94 meets the continuous wall 92 at a shoulder. The upper septum-engaging section 94 of the inner base member 68 is positioned relative to the outer base member 66 so as to compress the septum flange 80 between the section 94 and the rigid upper flange 84. This creates a fluid-tight seal between the base members 66 and 68, on the one hand, and the septum 74, on the other, and further tends to improve the resealing characteristics of the septum.

An outlet is provided the injection port 48, which extends from the injection chamber 88 exteriorly through the base members 66 and 68, to receive tubing 96 forming the injection port fluid outlet passageway 56. More specifically, the outlet includes a rigid outlet connector 98 which is integrally formed with the inner base member 68. The outlet connector 98 provides a passageway for fluid injected into the injection chamber 88, to pass out of the injection chamber, through the passageway 56, to either the reservoir 22 or the pump 50.

The pump 50, which can receive fluids from either the reservoir 22 or the injection port 48 through the recharge fluid flow passageway 54, comprises a resiliently flexible crown 100 integrally formed with the dome 62 of the injection port 48. The reinforced sheet 64 extends below all three primary components of the control assembly 28, and a rigid floor plate 102 overlies the reinforced sheet 64 beneath the pump and valve components of the control assembly. A pumping chamber 104 is defined between the crown 100 and the floor plate 102, and preferably has an evacuation capacity of one milliliter. Importantly, for purposes of the embodiment shown, the crown 100 is resiliently biased to generally maintain a dome or arch-shape, but can be deformed to lie substantially flat against the floor plate 102. The volume of the pumping chamber 104 can be customized to accommodate various intended uses for the system 20 and the required dosage to be infused into the patient per pumping stroke. By constructing the crown 100 of the same material as the septum 74, medication can be injected, if necessary, directly into the pumping chamber 104. In this case, the floor plate 102 functions as a needle guard, and the puncture site will tend to close upon itself and seal when the needle 78 is removed. The pump 50 further includes a pump inlet 106 which communicates with the recharge fluid flow passageway 54, and a pump outlet 108 in fluid communication with an inlet to the normally closed valve 52.

The recharge fluid flow passageway 54 provides means for conducting pump recharge fluid from either the injection port 48 or the reservoir 22 into the pumping chamber 104. The recharge fluid flow passageway 54 directs the recharge fluid over the top of the normally closed valve 52 before directing it into the pump inlet 106. This configuration is desirable in order to permit occlusion of a portion of the recharge passageway 54 when the outer housing for the normally closed valve 52 is pressed downwardly to open the normally closed valve. Additionally, positioned within the recharge passageway 54 are means for restricting the rate of fluid flow through the recharge passageway, which effectively limits the amount of recharge fluid permitted to enter the pumping chamber 104 over a given period of time.

More particularly, in normal operation after fluid is flushed from the pumping chamber 104 through the pump outlet 108 and through the normally closed valve 52 which has been opened, the valve is immediately shut by the removal of percutaneous pressure therefrom. Closure of the valve 52 prevents back flow of fluid through the valve into the pumping chamber 104. Since the crown 100 is resiliently biased towards its dome-like configuration, a pressure differential is created in the pumping chamber 104 relative to the fluid pressure in the reservoir 22, which tends to draw recharge fluid into the pumping chamber 104 until the crown 100 returns to its dome-like shape.

In one embodiment of the invention illustrated in FIGS. 4 through 8, the means for restricting the rate of fluid flow through the recharge passageway 54 comprises a capillary restrictor 110 (FIGS. 7 and 8) which provides a plurality of capillary-like fluid pathways through which the recharge fluid must pass before entering the pumping chamber 104. The capillary restrictor 110 includes a lower sheet 112 having a generally planar upper surface, and an upper sheet 114 having a plurality of grooves 116 extending from one end of the capillary restrictor 110 to the other. The capillary restrictor 110 is positioned within the recharge passageway 54 to overlie the normally closed valve 52 so that manual manipulation of the normally closed valve to open it to fluid flow simultaneously compresses the restrictor 110 to effectively occlude the recharge passageway 54.

Figure 9:
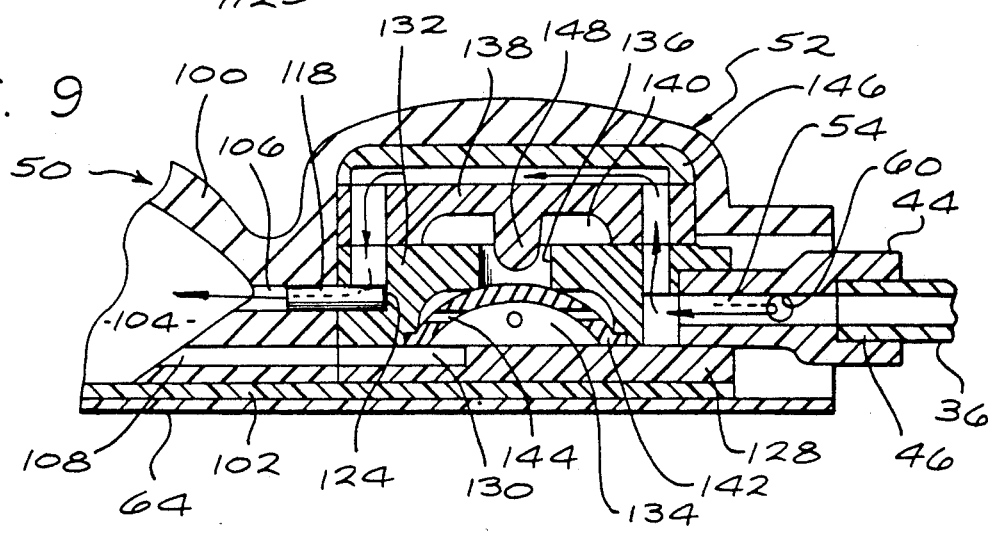
FIG. 9 is an enlarged fragmented sectional view taken generally along the line 4—4 of FIG. 2, illustrating, in contrast with FIGS. 4 through 8, the positioning of a second type of flow restrictor in the recharge fluid flow path, wherein the flow restrictor occludes a plurality of wicking fibers encased within a cylindrical impermeable housing.
Figure 10:
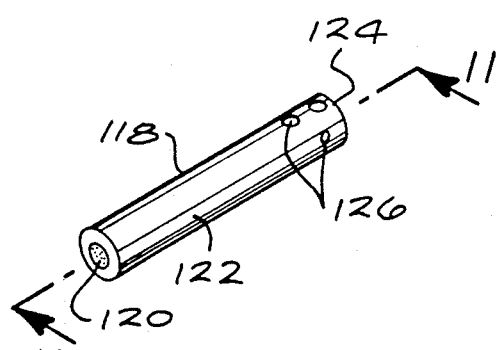
FIG. 10 is an enlarged perspective view of the wick restrictor illustrated in FIG. 9.
Figure 11:
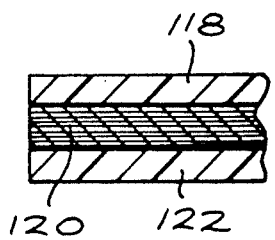
FIG. 11 is an enlarged, fragmented sectional view of the wick restrictor taken generally along the line 11—11 of FIG. 10.

In another embodiment of the invention illustrated in FIGS. 9 through 11, the means for restricting the rate of fluid flow through the recharge passageway 54 includes a wick restrictor 118 positioned to partly occupy the pump inlet 106. The wick restrictor 118 includes a plurality of wicking fibers 120 situated within an impermeable, cylindrical wick housing 122. The wick restrictor 118 is positioned within the recharge passageway 54 to ensure that all fluid drawn into the pumping chamber 104 must first pass through the restrictor 118. In this regard, one end 124 of the wick housing 122 is occluded, for example by means of a silicone sealer, and a plurality of apertures 126 are provided through the cylindrical wall of the housing 122 to provide an inlet for the wick restrictor 118. Recharge fluid is then caused to enter the wick restrictor 118 in a direction perpendicular of the length of the fibers 120, and then seep through the fibers before being permitted to pass into the pumping chamber 104.

The normally closed valve 52 includes a relatively rigid diaphragm support 128 affixed to a portion of the floor plate 102, which provides an inlet 130 for the valve. A rigid diaphragm cap 132 is supported upon the diaphragm support 128 and defines, with the diaphragm support, an inlet chamber 134 in fluid communication with the pumping chamber 104, and a valve passageway 136 (formed by the diaphragm cap 132). A resiliently flexible valve roof 138 is situated over the diaphragm cap 132 to define, with the cap, an outlet chamber 140 which overlies the inlet chamber 134. The valve passageway 136 provides a fluid flow pathway between the inlet chamber 134 and the outlet chamber 140.

A resiliently flexible valve diaphragm 142, constructed to form a dome-shaped member, is seated circumferentially upon the diaphragm support 128 within the inlet chamber 134 so that a portion of the diaphragm is normally positioned adjacent to the valve passageway 136. The valve diaphragm 142 is provided a plurality of diaphragm apertures 144. Unless forcibly displaced away from the portion of the cap 132 surrounding the valve passageway 136, the diaphragm 142 forms a seal which prevents any fluid flow through the normally closed valve 52. It is preferred that the cap 132 and the diaphragm 142 be constructed of materials which will not stick to one another, particularly after long periods of storage.

Figure 6:
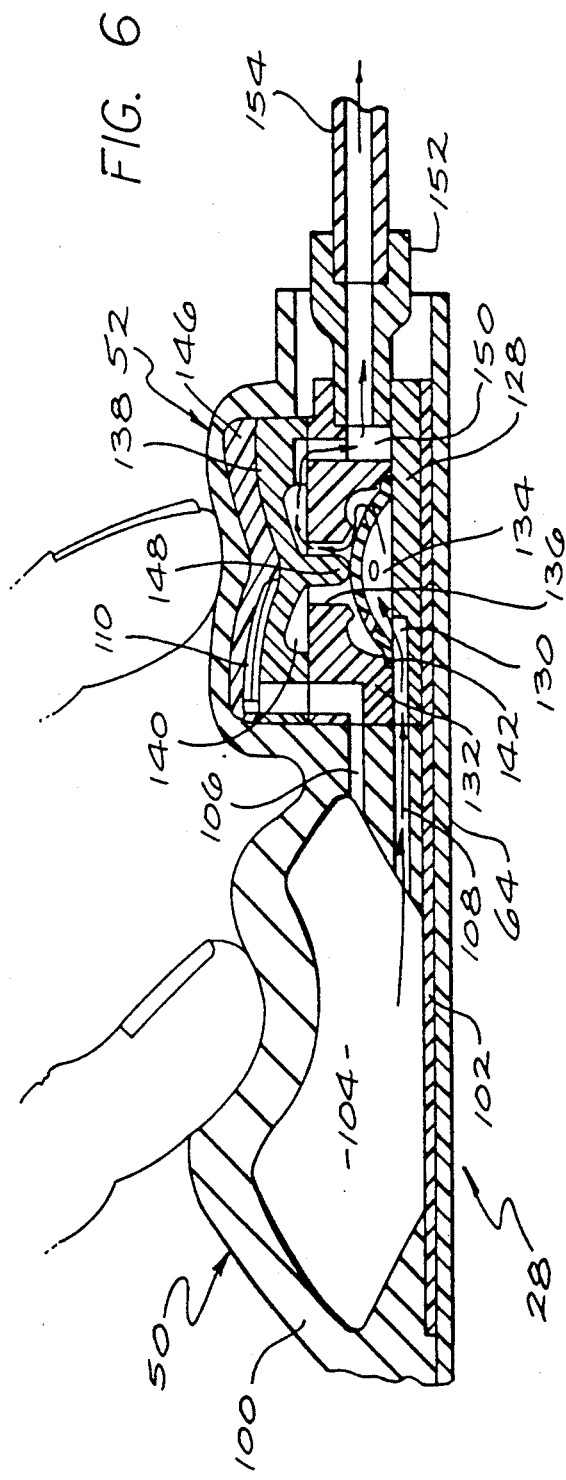
FIG. 6 is a fragmented sectional view of a portion of the control assembly similar to that illustrated in FIG. 5, illustrating the manner in which percutaneous pressure is utilized to open a normally closed valve and then flush discharged fluids from a pumping chamber within the pump.
Figure 7:
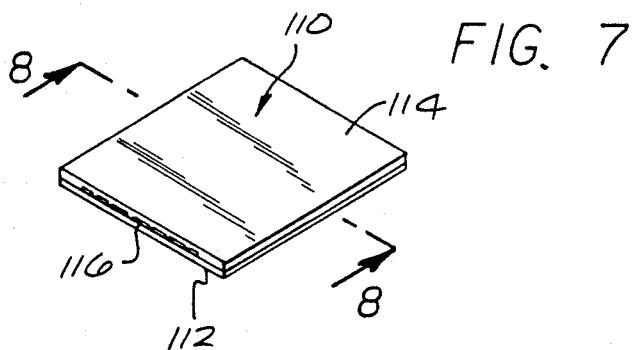
FIG. 7 is an enlarged perspective view of a flow restrictor positioned to generally overlie the normally closed valve in the recharge fluid flow path, which flow restrictor limits the rate at which the pump is recharged to restrict the total amount medication which can be pumped into the catheter over a given period of time.
Figure 8:
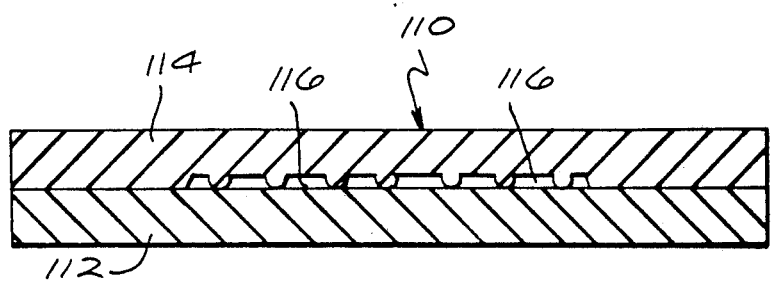
FIG. 8 is an enlarged sectional view of the flow restrictor taken generally along the line 8—8 of FIG. 7.

Some exterior surfaces of the diaphragm support 128, the cap 132 and the roof 138 define portions of the recharge passageway 54. A valve housing 146 also defines portions of the recharge passageway 54. A portion of the valve roof 138 overlying the outlet chamber 140 includes a downwardly extending diaphragm displacement finger 148 positioned directly above the valve passageway 136. The displacement finger 148 is situated for travel through the valve passageway 136 when pressed downwardly, and the diameter of the finger is small enough to prevent occlusion of the valve passageway 136 when the finger is pressed therethrough. When enough pressure is applied, the finger 148 causes the valve diaphragm 142 to flex downwardly a sufficient distance to break the valve seal and allow fluid to pass through the valve passageway 136 (FIG. 6). The housing 146, the valve roof 138 and the diaphragm 142 are each sufficiently resilient to return to their normal configurations and, consequently, close the normally closed valve 52 to fluid flow when the deforming pressure is removed. The inclusion of such a normally closed valve 52 in the system 20 enhances the system's utility and safety by preventing the flow of fluid through a discharge fluid flow conduit, partially defined by the normally closed valve 52, in the absence of direct, selectively applied percutaneous pressure on the control assembly 28.

A valve outlet 150 receives fluid from the outlet chamber 140 and directs it into a second control assembly port 152. As shown best in FIGS. 5 and 6, fixed within the second port 152 is second segment of surgical tubing 154 which conducts fluids discharged from the pumping chamber 104 from the control assembly 28 to the catheter 26.

The catheter 26 is preferably formed of a barium-impregnated silicone elastomer material which is radiopaque for detection by X-ray photography. A catheter inlet 156 is attached to the second segment of surgical tubing 154, and fluid medication exiting the control assembly 28 is directed by the catheter 26 for infusion into a specific portion of the body. For example, in the case of terminally ill patients a catheter 26 can be inserted into the lateral ventricle of the patient's brain. When such catheter placement is contemplated, a catheter clip 158, as shown in FIG. 1, can be advantageously utilized to hold the catheter 26 in place adjacent to a burr hole through the skull.

Although the injection port 48, the pump 50 and the normally closed valve 52 are shown in the exemplary drawings as combined to form the unitary control assembly 28, each component may be separately constructed to form individual system components which can be connected to one another by a conduit such as flexible surgical tubing.

In use, the medication infusion system 20 provides a convenient means for percutaneously controlling the flow of fluid through the subcutaneously implanted infusion system, and yet includes important safety features which prevent the inadvertent, accidental infusion of medication, and further limits the maximum amount of medication which can be infused through the system over a given time period. To use the system 20, it must first be subcutaneously implanted. Preferably, the control assembly 28 is placed over a hard boney surface to provide sufficient resistance to percutaneous pressure which will be applied thereto. Often, when initially implanted, the system 20 has previously been primed with a sterile saline solution which must be evacuated and replaced with the desired medication.

Medication is introduced into the infusion system 20 through injection into the injection chamber 88 of the injection port 48. Medication injected into the injection chamber 88 flows through the injection port fluid outlet passageway 56 to the port 60 which intersects with a portion of the recharge fluid flow passageway 54. Here, the injected medication will take the path of least resistance to either fill the reservoir 22 or the pumping chamber 104. When filling the reservoir 22, the fluid medication flows out of the control assembly 28 through the first control assembly port 44, through the first segment of surgical tubing 36 connecting the control assembly to the reservoir, and through the outlet connector 34 fixed within the reservoir aperture 32.

If the pump crown 100 has been depressed to flush priming fluid from the pumping chamber 104, it will attempt to regain its original dome shape. This will create a pressure differential, assuming the normally closed valve 52 is closed, which will draw medication through the recharge fluid flow passageway 54 from either the injection chamber 88 or the reservoir 22. The fluid flow restrictor, whether it be the capillary restrictor 110 or the wick restrictor 118, effectively limits the rate at which the pumping chamber 104 is permitted to draw-in recharge fluids.

To begin the infusion of medication to the patient through the system 20, the normally closed valve 52 must be opened by applying percutaneous pressure thereto, to permit medication in the pumping chamber 104 to be discharged through the pump outlet 108. The normally closed valve 52 is opened by manually applying percutaneous downward pressure to the valve housing 146 (FIG. 6). Such downward percutaneous pressure occludes the recharge passageway 54 and forces the displacement finger 148 downwardly through the valve passageway 136 to disengage the valve diaphragm 142 from the valve seat. Thus, by simply pressing downwardly on the valve housing 146, a discharge fluid conduit is opened through the valve 52 to permit medication to be flushed from the pump 50, while simultaneously occluding the recharge passageway 54 and thereby preventing any fluid flow out of the pump inlet 106. When using the capillary restrictor illustrated in FIGS. 7 and 8, the upper sheet 114 collapses upon the lower sheet 112 to occlude the capillary-like grooves 116. When the wick restrictor 118 is utilized (FIGS. 9 through 11), the channelling of recharge fluid over the top of the valve 52 permits a portion of the recharge passageway 54 to be occluded by the same downward finger pressure.

With the valve 52 opened, medication in the pumping chamber 104 can be discharged through the pump outlet 108 and the normally closed valve 52 by applying downward percutaneous pressure to the pump 50. This is accomplished by pressing the pump crown 100 downwardly to collapse the pump crown against the floor plate 102. Medication within the pumping chamber 104 is caused to flow from the pump outlet 108 through the valve to the second control assembly port 152, and into the second segment of surgical tubing 154 for delivery to the catheter 26.

After the medication is flushed from the pumping chamber 104, the valve 52 is closed by simply removing the percutaneous pressure applied thereto, and the recharge passageway 54 is opened to permit fluid flow into the pump 50 when the valve is closed. The steps of closing the valve 52 and opening the recharge passageway 54 occur simultaneously upon the withdrawal of percutaneous pressure from the valve. The pump crown 100 thereafter attempts to regain its original dome-shaped configuration, drawing recharge fluid into the pumping chamber 104 at a rate controlled by either the capillary restrictor 110 or the wick restrictor 118.

The medication infusion system 20 described above can greatly ease the burden of medical personnel and hospital facilities by providing means for internally storing a large quantity of medication which is to be administered to a patient over an extended period of time. Moreover, various apparatuses can be added to the system 20 for a multitude of purposes, such as the provision of a burr hole reservoir situated adjacent to the skull to facilitate injection of medications directly into the brain.

Although two particular embodiments of the invention have been described in detail for purposes of illustration, various modifications of each may be made without departing from the spirit and scope of the invention. Accordingly, the invention is not to be limited, except as by the appended claims.

We claim:

1. A fluid control assembly, comprising:
 a self-recharging, manually actuable pump for discharging a measured amount of fluid from a pumping chamber,
 means for conducting pump recharge fluid into the pumping chamber;
 means for conducting discharge fluid from the pumping chamber;
 valve means, actuable by manual percutaneous manipulation, for controlling the flow of discharge fluid from the pumping chamber, the valve means forming a portion of the discharge fluid conducting means, the valve means including a normally closed valve having a resiliently flexible body which defines a fluid flow passageway therethrough, a valve member positioned within the fluid flow passageway to occlude the valve means, a valve inlet in fluid communication with the pumping chamber, a valve outlet, and a valve passageway situated between the valve inlet and outlet, wherein the valve member is resiliently biased to occlude the valve passageway, and wherein the recharge fluid conducting means extends at least partially through the valve body; and
 means for restricting the rate of fluid flow through the recharge fluid conducting means, wherein the restricting means limits the amount of recharge fluid permitted to enter into the pumping chamber over a given period of time, the restricting means including at least one capillary-like fluid pathway through which the recharge fluid must pass before entering the pumping chamber, wherein the restricting means is positioned relative to the valve means such that actuation of the valve means causes an occlusion of the restricting means to prevent fluid flow through the restricting means.

2. A fluid control assembly as set forth in claim 1, wherein the normally closed valve includes a displacement finger which is situated and configured to displace the valve member and open the valve means to fluid flow therethrough when the valve means is actuated by manual percutaneous manipulation.

3. A fluid control assembly as set forth in claim 2, wherein the restricting means is positioned relative to the displacement finger so that manipulation of the valve means to move the displacement finger, which opens the discharge fluid conducting means, occludes the at least one capillary-like fluid pathway to close the recharge fluid conducting means.

4. A fluid control assembly as set forth in claim 1, wherein the pump includes a pump inlet in fluid communication with the recharge fluid conducting means, a pump outlet in fluid communication with the discharge fluid conducting means, and a resilient crown overlying a floor plate to define the pumping chamber therebetween.

5. An infusion reservoir and pump system, comprising:
 means for receiving medication into the system by injection, including an injection port including an elastomeric outer housing having an integral elastomeric septum, a first base member situated within the outer housing and contiguously engaging a first peripheral portion of the septum, a second base member situated within the first base member and within the outer housing, wherein the second base member contiguously engages the first peripheral portion of the septum opposite to the first base member, such that the septum is compressed between the first and second base member, and an outlet extending from an internal chamber between the septum and the second base member, exteriorly through the outer housing;
 a reservoir fluidly connected to the receiving means in a manner permitting the subcutaneous transfer of medication from the receiving means to the reservoir;
 a catheter for directing the medication to a specific location in a body, the catheter having a catheter inlet and being positionable with the body independently of the position of the reservoir;
 means for conducting the medication from the reservoir to the catheter inlet;
 means for controlling the flow of medication from the reservoir to the catheter, the controlling means forming a portion of the conducting means and including normally closed valve means and a pump for flushing a measured quantity of medication into the catheter when the normally closed valve means is opened; and means for restricting the flow of medication from the reservoir to the pump, and this limiting the rate that pump is recharged, to restrict the total amount of medication which can be pumped into the catheter over a given period of time.

6. A system as set forth in claim 5, wherein the elastomeric outer housing of the injection port includes an upper dome attached to a lower reinforced sheet, the upper dome including a lower flange sealed to the reinforced sheet, a frusto-conical side wall extending upwardly from the lower flange, and the septum which is integrally formed with the side wall and supported thereby in spaced relation to the lower reinforced sheet.

7. A system as set forth in claim 6, wherein the first peripheral portion of the septum extends circumferentially outwardly from a body portion of the septum between the side wall and the lower reinforced sheet, and wherein the first base member comprises a generally frusto-conical ring configured to engage and support an interior surface of the side wall, and a rigid upper flange which overlies the first peripheral portion of the septum to provide a rigid barrier between the first peripheral portion of the septum and the adjacent side wall portions, wherein the upper flange circumscribes the septum and engages the first peripheral portion of the septum.

8. A system as set forth in claim 7, wherein the second base member is cup-shaped and includes a floor and a continuous wall which extends upwardly therefrom, wherein the continuous wall projects from the floor to engage an inner surface of the first base member in an interference fit, wherein the second base member, with the septum, defines an internal injection chamber and forms a needle shield adjacent to the lower reinforced sheet, the second base member including an upper septum-engaging section which extends upwardly from the continuous wall to underlie the first peripheral portion of the septum and compress the first peripheral portion of the septum between the upper flange of the first base member and the upper septum-engaging section of the second base member.

9. A system as set forth in claim 5, wherein the reservoir includes a flexible outer body capable of expanding to accommodate varying amounts of medication.

10. A system as set forth in claim 5, wherein the normally closed valve means includes a resiliently flexible body which defines a fluid flow passageway therethrough, a valve member positioned within the fluid flow passageway to occlude the valve means, a valve inlet in fluid communication with the pump, a valve outlet in fluid communication with the catheter inlet, and a valve passageway situated directly between the valve inlet and outlet, wherein the valve member is resiliently biased to occlude the valve passageway.

11. A system as set forth in claim 10, wherein the normally closed valve means includes a displacement finger which is situated and configured to displace the valve member and open the valve means to fluid flow therethrough when the valve means is actuated by manual percutaneous manipulation.

12. A system as set forth in claim 11, wherein the restricting means includes at least one capillary-like fluid pathway through which medication must pass before entering the pump, wherein the restricting means is positioned within the valve body relative to the displacement finger so that manipulation of the valve means to move the displacement finger occludes the at least one capillary-like fluid pathway to close that portion of the conducting means defined by the restricting means.

13. A system as set forth in claim 10, wherein the restricting means includes a wick restrictor having a plurality of wicking fibers situated within an impermeable wick housing, wherein the wick restrictor is positioned within a portion of the conducting means such that all fluid drawn into the pump must first pass through the wick restrictor.

14. A system as set forth in claim 13, wherein one end of the wick housing is occluded, and an inlet is provided adjacent to the occluded end through a wall of the wick housing.

15. A system as set forth in claim 5, wherein the pump includes a pump inlet in fluid communication with the reservoir, a pump outlet in fluid communication with the valve means, and a resilient crown overlying a floor plate to define a pumping chamber therebetween.

16. A subcutaneously implantable medication infusion control assembly having a medicament recharge restriction, comprising:

an injection port for receiving medication into the system by injection;

a self-recharging, manually actuable pump for discharging a measured amount of medication from a pumping chamber;

means for conducting pump recharge medication into the pumping chamber;

means for conducting discharge medication from the pumping chamber;

valve means, actuable by manual percutaneous manipulation, for controlling the flow of discharge medication from the pumping chamber, the valve means forming a portion of the discharge medication conducting means, the valve means including a normally closed valve having a resiliently flexible body which defines a fluid flow passageway therethrough, a valve member positioned within the fluid flow passageway to occlude the valve means, a valve inlet in fluid communication with the pumping chamber, a valve outlet, and a valve passageway situated between the valve inlet and the valve outlet, wherein the valve member is resiliently biased to occlude the valve passageway, and a displacement finger situated and configured to displace the valve member and open the valve means to fluid flow therethrough when the valve means is actuated by manual percutaneous manipulation; and means for restricting the rate of medication flow through the recharge medication conducting means, wherein the restricting means limits the amount of recharge medication permitted to enter into the pumping chamber over a given period of time;

wherein the recharge medication conducting means extends at least partially through the valve body.

17. A control assembly as set forth in claim 16, wherein the injection port comprises:

an elastomeric outer housing including an upper dome attached to a lower reinforced sheet, the upper dome including a lower flange sealed to the reinforced sheet, a frusto-conical side wall extending outwardly from the lower flange, and a septum integrally formed with the side wall and supported thereby in spaced relation to the lower reinforced sheet;

a rigid outer base member enclosed within the elastomeric outer housing, the outer base member including a rigid upper flange positioned to circumscribe the septum and engage a first peripheral portion of the septum; and a rigid inner base member enclosed within the elastomeric outer housing, the inner base member being situated within and engaging the outer base member in an interference fit to define, with the septum, an internal injection chamber and form a needle shield adjacent to the lower reinforced sheet, wherein the inner base member includes an upper septum-engaging section which engages the first peripheral portion of the septum opposite to the rigid upper flange to compress it therebetween.

18. A control assembly as set forth in claim 16, wherein the restricting means includes at least one capillary-like fluid pathway through which the recharge medication must pass before entering the pumping chamber, and wherein the restricting means is positioned relative to the displacement finger such that manipulation of the valve means to move the displacement finger, which opens the discharge medication conducting means, occludes the at least one capillary-like fluid pathway to close the recharge medication conducting means.

19. A control assembly as set forth in claim 16, wherein the restricting means includes a wick restrictor having a plurality of wicking fibers situated within an impermeable wick housing, the wick restrictor being positioned within a portion of the recharge medication conducting means so that all fluid drawn into the pumping chamber must first pass through the wick restrictor, wherein one end of the wick housing is occluded and an inlet is provided adjacent to the occluded end through a wall of the wick housing.

20. A process for infusing medication, the steps comprising:

implanting an infusion system constructed of materials suitable for extended subcutaneous emplacement in the body, the infusion system including a self-recharging, manually actuable pump having a pump inlet and a pump outlet, and a normally closed valve actuable by manual percutaneous manipulation for controlling the flow of fluid from the pump;

receiving medication into the system by injection;

storing the injected medication;

opening the normally closed valve by applying percutaneous pressure thereto, to permit medication in the pump to be discharged through the pump outlet;

occluding the pump inlet to prevent medication from entering the pump when the normally closed valve is opened;

discharging medication in the pump through the pump outlet and the normally closed valve, by applying percutaneous pressure to the pump;

closing the normally closed valve by removing the percutaneous pressure applied thereto;

opening the pump inlet to permit fluid flow into the pump when the normally closed valve is closed; and restricting the rate at which fluid can flow into the pump through the pump inlet by causing fluid stored in the infusion system to pass through a plurality of packed wicking fibers.

21. An infusion process as set forth in claim 20, wherein the steps of opening the normally closed valve and occluding the pump inlet are accomplished simultaneously through the application of percutaneous pressure to the normally closed valve.

22. An infusion process as set forth in claim 21, wherein the step of opening the normally closed valve includes the step of pressing a housing of the normally closed valve downwardly.

23. An infusion process as set forth in claim 21, wherein the step of discharging medication in the pump includes the step of pressing a housing of the pump downwardly to flush fluid from a pumping chamber within the pump.

24. An infusion process as set forth in claim 20, wherein the step of flushing fluid from the pump occurs only after the step of opening the normally closed valve.

25. An infusion process as set forth in claim 23, wherein the steps of closing the normally closed valve and opening the pump inlet are accomplished simultaneously through the withdrawal of percutaneous pressure from the normally closed valve.

26. An infusion process as set forth in claim 20, wherein the step of causing fluid stored in the infusion system to pass through a plurality of packed wicking fibers includes the steps of placing the wicking fibers in a fluid flow conduit between the pump and the stored medication, and introducing the medication perpendicularly to the length of the wicking fibers.

27. A process for percutaneously controlling the flow of fluid through a subcutaneously implanted infusion system including a manually actuable pump having a pump inlet and a pump outlet, and a valve for controlling the flow of fluid from the pump, the process steps comprising:

opening the valve by applying percutaneous pressure thereto, to permit medication in the pump to be discharged through the pump outlet;

occluding the pump inlet to prevent medication from entering the pump when the valve is opened;

discharging medication in the pump through the pump outlet and the valve, by applying percutaneous pressure to the pump;

closing the valve by removing the percutaneous pressure applied thereto;

opening the pump inlet to permit fluid flow into the pump when the valve is closed; and restricting the rate at which fluid can flow into the pump through the pump inlet by placing packed wicking fibers in or adjacent to the pump inlet such that inlet fluid to the pump is caused to first pass through the packed wicking fibers, and wherein the fluid is introduced perpendicularly to the length of the wicking fibers.

28. A process as set forth in claim 27, wherein the steps of opening the normally closed valve and occluding the pump inlet are accomplished simultaneously through the application of percutaneous pressure to the valve.

29. A process as set forth in claim 28, wherein the step of opening the valve by applying percutaneous pressure thereto includes the step of pressing a housing of the valve downwardly, and wherein the step of discharging medication in the pump includes the step of pressing a housing of the pump downwardly to flush fluid from a pumping chamber within the pump.

30. A process as set forth in claim 29, wherein the step of flushing fluid from the pump occurs only after the step of opening the valve.

31. A process as set forth in claim 27, wherein the steps of closing the valve by removing the percutaneous pressure and opening the pump inlet are accomplished simultaneously through the withdrawal of percutaneous pressure from the valve.

32. A process for percutaneously controlling the flow of fluid through a subcutaneously implanted infusion system including a manually actuable pump having a pump inlet and a pump outlet, and a normally closed valve for controlling the flow of fluid from the pump, the process steps comprising:

opening the normally closed valve by pressing a housing of the normally closed valve downwardly, to permit medication in the pump to be discharged through the pump outlet;

occluding the pump inlet to prevent medication from entering the pump when the normally closed valve is opened, wherein the steps of opening the normally closed valve and occluding the pump inlet are accomplished simultaneously through the application of percutaneous pressure to the normally closed valve;

discharging medication in the pump through the pump outlet and the normally closed valve, by applying percutaneous pressure to the pump, wherein the step of discharging medication in the pump includes the step of pressing a housing of the pump downwardly to flush fluid from a pumping chamber within the pump, wherein the step of flushing the fluid from the pump occurs only after the step of opening the normally closed valve;

closing the normally closed valve by removing the percutaneous pressure applied thereto;

opening the pump inlet to permit fluid flow into the pump when the normally closed valve is closed, wherein the steps of closing the normally closed valve and opening the pump inlet are accomplished simultaneously through the withdrawal of percutaneous pressure from the normally closed valve; and restricting the rate at which fluid can flow into the pump through the pump inlet by placing a plurality of packed wicking fibers in the pump inlet or in a fluid flow conduit adjacent to the pump inlet, introducing pump inlet fluid perpendicularly to the length of the wicking fibers, and causing the fluid to pass therethrough prior to entering the pump.

33. A fluid control assembly, comprising:

a self-recharging, manually actuable pump for discharging a measured amount of fluid from a pumping chamber;

means for conducting pump recharge fluid into the pumping chamber;

means for conducting discharge fluid from the pumping chamber;

valve means, actuable by manual percutaneous manipulation, for controlling the flow of discharge fluid from the pumping chamber, the valve means forming a portion of the discharge fluid conducting means, the valve means including a normally closed valve having a resiliently flexible body which defines a fluid flow passageway therethrough, a valve member positioned within the fluid flow passageway to occlude the valve means, a valve inlet in fluid communication with the pumping chamber, a valve outlet, a valve passageway situated between the valve inlet and outlet, wherein the valve member is resiliently biased to occlude the valve passageway, and a displacement finger which is situated and configured to displace the valve member and open the valve means to fluid flow therethrough when the valve means is actuated by manual percutaneous manipulation; and means for restricting the rate of fluid flow through the recharge fluid conducting means, wherein the restricting means limits the amount of recharge fluid permitted to enter into the pumping chamber over a given period of time, the restricting means including at least one capillary-like fluid pathway through which the recharge fluid must pass before entering the pumping chamber, wherein the restricting means is positioned relative to the valve means such that actuation of the valve means causes an occlusion of the restricting means to prevent fluid flow through the restricting means, and wherein the restricting means is positioned relative to the displacement finger so that manipulation of the valve means to move the displacement finger, which opens the discharge fluid conducting means, occludes the at least one capillary-like fluid pathway to close the recharge fluid conducting means.

34. A fluid control assembly, comprising:

a self-recharging, manually actuable pump for discharging a measured amount of fluid from a pumping chamber;

means for conducting pump recharge fluid into the pumping chamber;

means for conducting discharge fluid from the pumping chamber;

valve means, actuable by manual percutaneous manipulation, for controlling the flow of discharge fluid from the pumping chamber, the valve means forming a portion of the discharge fluid conducting means; and means for restricting the rate of fluid flow through the recharge fluid conducting means, wherein the restricting means limits the amount of recharge fluid permitted to enter into the pumping chamber over a given period of time, the restricting means comprising a wick restrictor, including a plurality of wicking fibers situated within an impermeable wick housing, and wherein the wick restrictor is positioned within a portion of the recharge fluid conducting means so that all fluid drawn into the pumping chamber must first pass through the wick restrictor.

35. A fluid control assembly as set forth in claim 34, wherein one end of the wick housing is occluded, and an inlet is provided adjacent to the occluded end through a wall of the wick housing.

36. An infusion reservoir and pump system, comprising:

means for receiving medication into the system by injection;

a reservoir fluidly connected to the receiving means in a manner permitting the subcutaneous transfer of medication from the receiving means to the reservoir;

a catheter for directing the medication to a specific location in a body, the catheter having a catheter inlet and being positionable within the body independently of the position of the reservoir;

means for conducting the medication from the reservoir to the catheter inlet;

means for controlling the flow of medication from the reservoir to the catheter, the controlling means forming a portion of the conducting means and including normally closed valve means and a pump for flushing a measured quantity of medication into the catheter when the normally closed valve means is opened, the normally closed valve means including a resiliently flexible body which defines a fluid flow passageway therethrough, a valve member positioned within the fluid flow passageway to occlude the valve means, a valve inlet in fluid communication with the pump, a valve outlet in fluid communication with the catheter inlet, a valve passageway situated directly between the valve inlet and outlet, wherein the valve member is resiliently biased to occlude the valve passageway, and a displacement finger which is situated and configured to displace the valve member and open the valve means to fluid flow therethrough when the valve means is actuated by manual percutaneous manipulation; and means for restricting the flow of medication from the reservoir to the pump, and thus limiting the rate the pump is recharged, to restrict the total amount of medication which can be pumped into the catheter over a given period of time, wherein the restricting means includes at least one capillary-like fluid pathway through which medication must pass before entering the pump, wherein the restricting means is positioned within the valve body relative to the displacement finger so that manipulation of the valve means to move the displacement finger occludes the at least one capillary-like fluid pathway to close that portion of the conducting means defined by the restricting means.

37. A system as set forth in claim 36, wherein the pump includes a pump inlet in fluid communication with the reservoir, a pump outlet in fluid communication with the valve means, and a resilient crown overlying a floor plate to define a pumping chamber therebetween.

38. An infusion reservoir and pump system, comprising:

means for receiving medication into the system by injection;

a reservoir fluidly connected to the receiving means in a manner permitting the subcutaneous transfer of medication from the receiving means to the reservoir;

a catheter for directing the medication to a specific location in a body, the catheter having a catheter inlet and being positionable with the body independently of the position of the reservoir;

means for conducting the medication from the reservoir to the catheter inlet;

means for controlling the flow of medication from the reservoir to the catheter, the controlling means forming a portion of the conducting means and including normally closed valve means and a pump for flushing a measured quantity of medication into the catheter when the normally closed valve means is opened, the normally closed valve means including a resiliently flexible body which defines a fluid flow passageway therethrough, a valve member positioned within the fluid flow passageway to occlude the valve means, a valve inlet in fluid communication with the pump, a valve outlet in fluid communication with the catheter inlet, and a valve passageway situated directly between the valve inlet and outlet, wherein the valve member is resiliently biased to occlude the valve passageway; and means for restricting the flow of medication from the reservoir to the pump, and thus limiting the rate the pump is recharged, to restrict the total amount of medication which can be pumped into the catheter over a given period of time, the restricting means including a wick restrictor having a plurality of wicking fibers situated within an impermeable wick housing, wherein the wick restrictor is positioned within a portion of the conducting means such that all fluid drawn into the pump must first pass through the wick restrictor.

39. A system as set forth in claim 38, wherein one end of the wick housing is occluded, and an inlet is provided adjacent to the occluded end through a wall of the wick housing.

40. A fluid control assembly, comprising:

a self-recharging, manually actuable pump for discharging a measured amount of fluid from a pumping chamber;

means for conducting pump recharge fluid into the pumping chamber;

means for conducting discharge fluid from the pumping chamber;

valve means, actuable by manual manipulation, for controlling the flow of discharge fluid from the pumping chamber, the valve means forming a portion of the discharge fluid conducting means, wherein the valve means includes a normally closed valve having a resiliently flexible body which defines a fluid flow passageway therethrough, a valve member positioned within the fluid flow passageway to occlude the valve means, a valve inlet in fluid communication with the pumping chamber, a valve outlet, and a valve passageway situated between the valve inlet and outlet, wherein the valve member is resiliently biased to occlude the valve passageway, and wherein the normally closed valve includes a displacement finger which is situated and configured to displace the valve member and open the valve means to fluid flow therethrough when the valve means is actuated by manual manipulation; and means for severely restricting the rate of fluid flow through the recharge fluid conducting means in comparison with the rate at which fluid would otherwise flow therethrough, wherein the restricting means limits the amount of recharge fluid permitted to enter into the pumping chamber over a given period of time to a know flow rate, wherein the restricting means includes a capillary-like fluid pathway defining a portion of the recharge fluid conducting means, and wherein the restricting means is positioned relative to the displacement finger so that manipulation of the valve means to move the displacement finger, which opens the discharge fluid conducting means, occludes the capillary-like fluid pathway to close the recharge fluid conducting means.

41. A process for controlling the flow of fluid through an infusion system including a manually actuable pump having a pump inlet and a pump outlet, and a valve for controlling the flow of fluid from the pump, the process steps comprising:

opening the valve by applying pressure thereto, to permit medication in the pump to be discharged through the pump outlet;

occluding the pump inlet to prevent medication from entering the pump when the valve is opened;

discharging medication in the pump through the pump outlet and the valve, by applying pressure to the pump;

closing the valve by removing the pressure applied thereto;

opening the pump inlet to permit fluid flow into the pump when the valve is closed; and restricting the rate at which fluid can flow into the pump through the pump inlet, including the steps of causing inlet fluid to pass through a capillary-like fluid pathway as the fluid is drawn into the pump, wherein the capillary-like fluid pathway severely restricts the rate at which fluid would otherwise flow into the pump to a known flow rate that limits the amount of fluid which can be pumped through the system over a given period of time, wherein the step of occluding the pump inlet includes the step of closing the capillary-like fluid pathway by the pressure applied to open the valve.

42. An infusion reservoir and pump system, comprising:

means for receiving medication into the system by injection;

a reservoir fluidly connected to the receiving means in a manner permitting the subcutaneous transfer of medication from the receiving means to the reservoir;

a catheter for directing the medication to a specific location in a body, the catheter having a catheter inlet and being positionable within the body independently of the position of the reservoir;

means for conducting the medication from the reservoir to the catheter inlet;

means for controlling the flow of medication from the reservoir to the catheter, the controlling means forming a portion of the conducting means and including normally closed valve means and a pump for flushing a measured quantity of medication into the catheter when the normally closed valve means is opened, the normally closed valve means including a resiliently flexible body which defines a fluid flow passageway therethrough, a valve member positioned within the fluid flow passageway to occlude the valve means, a valve inlet in fluid communication with the pump, a valve outlet in fluid communication with the catheter inlet, a valve passageway situated directly between the valve inlet and outlet, wherein the valve member is resiliently biased to occlude the valve passageway, and a displacement finger which is situated and configured to displace the valve member and open the valve means to fluid flow therethrough when the valve means is actuated by manual percutaneous manipulation; and means for restricting the flow of medication from the reservoir to the pump, and thus limiting the rate the pump is recharged, to restrict the total amount of medication which can be pumped into the catheter over a given period of time, wherein the restricting means includes a wick restrictor having a plurality of wicking fibers situated within an impermeable wick housing, wherein the wick restrictor is positioned within a portion of the conducting means such that all fluid drawn into the pump must first pass through the wick restrictor.

* * * * *

UNITED STATES PATENT AND TRADEMARK OFFICE
CERTIFICATE OF CORRECTION

PATENT NO. : 5,152,753

DATED : October 6, 1992

INVENTOR(S) : Stephen W. Laguette, Gary P. East, David A. Watson and Thomas J. Carlisle It is certified that error appears in the above-identified patent and that said Letters Patent is hereby corrected as shown below:

In column 14, line 50, delete "member" and insert therefor --members--.

In column 15, line 4, delete "this" and insert therefor --thus--.

In column 15, line 5, delete "that" and insert therefor --the--.

In column 18, line 17, delete "20" and insert therefor --23--.

In column 21, line 58, delete "with" and insert therefor --within--.

Signed and Sealed this

Fourteenth Day of September, 1993

Attest:

BRUCE LEHMAN

*Attesting Officer*     *Commissioner of Patents and Trademarks*